United States Patent [19]

Haacke et al.

[11] Patent Number: 4,516,429

[45] Date of Patent: May 14, 1985

[54] METHOD FOR TESTING THE TOTAL LENGTH OF EXTENDED ROUND MATERIAL SUCH AS PIPES AND BARS, AND DEVICE TO CARRY OUT THE METHOD

[75] Inventors: Harri Haacke, Dusseldorf; Karl Loch, Duisburg, both of Fed. Rep. of Germany

[73] Assignee: Mannesmann Aktiengesellschaft, Dusseldorf, Fed. Rep. of Germany

[21] Appl. No.: 354,664

[22] Filed: Mar. 4, 1982

[30] Foreign Application Priority Data

Apr. 9, 1981 [DE] Fed. Rep. of Germany ....... 3114850

[51] Int. Cl.$^3$ ............................................. G01N 29/04
[52] U.S. Cl. ......................................... 73/638; 324/262
[58] Field of Search ...................... 73/432 R, 622, 638, 73/639, 432 B; 324/52, 262, 243, 261; 378/59, 55

[56] References Cited

U.S. PATENT DOCUMENTS

| | | | |
|---|---|---|---|
| 3,375,706 | 4/1968 | Pandelis et al. | 73/622 |
| 4,217,782 | 8/1980 | Pont | 73/638 |
| 4,375,165 | 3/1983 | de Sterke | 73/622 |
| 4,387,598 | 6/1983 | Jamieson et al. | 73/622 |

*Primary Examiner*—Stewart J. Levy
*Assistant Examiner*—Hezron E. Williams
*Attorney, Agent, or Firm*—Oldham, Oldham & Weber Co.

[57] ABSTRACT

A method and apparatus for testing the entire length of round material, such as pipes, helically moving in a longitudinal direction. Testing mechanisms are maintained along the path of the pipe and are adapted to move with the pipe to test the pipe in motion. The testing mechanisms are transported fixed distances and returned to starting positions to again move with the pipe such that each testing mechanism tests finite segments of the pipe, the testing mechanisms being so spaced as to assure that the entire pipe is tested. Such testing in motion prevents any untested areas from existing on the pipe.

1 Claim, 7 Drawing Figures

METHOD FOR TESTING THE TOTAL LENGTH OF EXTENDED ROUND MATERIAL SUCH AS PIPES AND BARS, AND DEVICE TO CARRY OUT THE METHOD

The invention relates to a method for testing the total length of extended round material, moving helically in longitudinal direction, such as pipes and bars. A typical such test is that of ultrasonic testing in segment immersion, detecting longitudinal and transverse faults, as well as wall thickness.

In the testing of extended rolling material it was customary up to now to carry out the testing with testing apparatus fixed in axial direction. The disadvantage of this testing method in the testing of individual pieces lies in that both at the beginning and end of the pipe, the wedges occuring through rotation and thrust of the pipe remain unchecked.

This means that an additional checking of these unchecked pipe ends must take place.

For small dimensions, to avoid unchecked end portions, impact by impact testing is known; however, here too, an unchecked wedge remains at the beginning of the first and the end of the last pipe. Because of the axial and radial tolerances which are preferably present in heat-finished test material of larger dimensions, the impact by impact method is, however, not practicable in terms of testing technique. This also applies to pipes, the ends of which are provided with welding stages, since in the impact by impact method there is a risk of damage to the pipe ends.

The object of the invention is to create a method and devices to test extended round material such as pipes and bars, by means of which the material to be tested can be tested from the beginning to the end.

To solve this problem a method and devices are proposed, as described hereinafter.

The advantages of the method according to the invention lie in that re-checking can be dispensed with even in testing individual pieces.

A possible form of embodiment is shown in diagrammatic form in the enclosed drawings, for a device according to the invention.

Figure 1A:
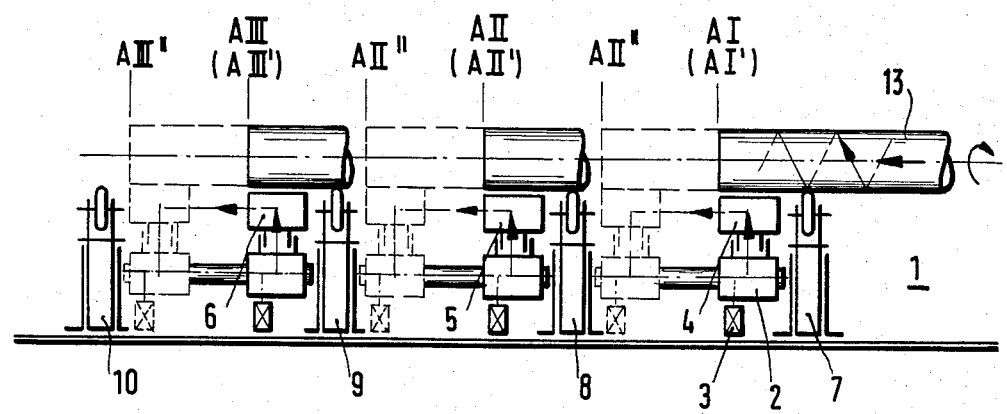
FIGS. 1a–1c shows a longitudinal section through the conveying system of a testing installation, with the positions shown for the engagement of the beginning and end of test material.

In FIG. 1a the mechanical part of a testing installation 1 is represented in simplified form, in which the test material 13 is transported rotating about its longitudinal axis on tilted radial rolls 7,8,9,10 in axial direction. Between the radial rolls 7,8,9,10 testing mechanisms heads or probes 4,5,6 are arranged, which are movable parallel to the longitudinal axis of the test material 13 in both directions on electromotively movable slide carriages 2.

Figure 1B:
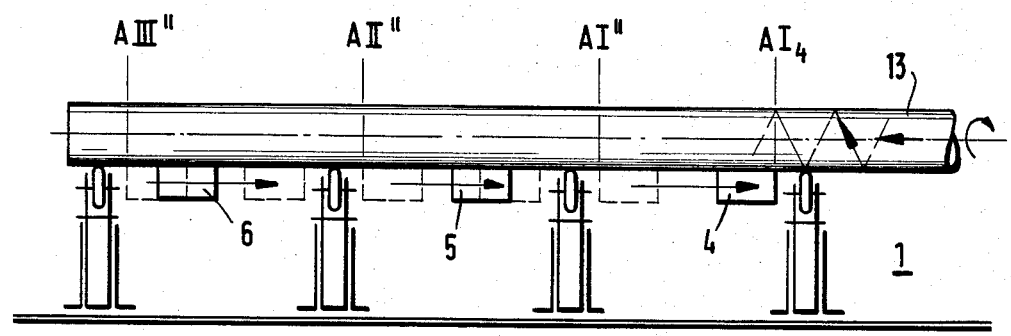
Figure 1C:
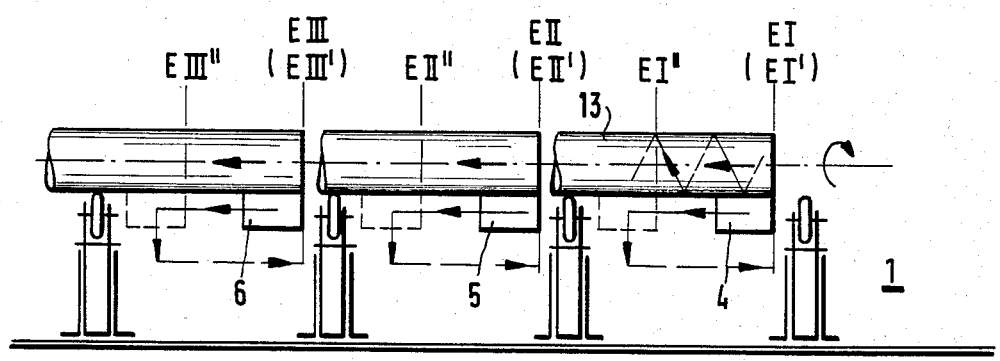

The movement cycles of test material 13 and testing mechanisms corresponding to the method according to the invention are indicated in FIGS. 1a to 1c.

Figure 2A:
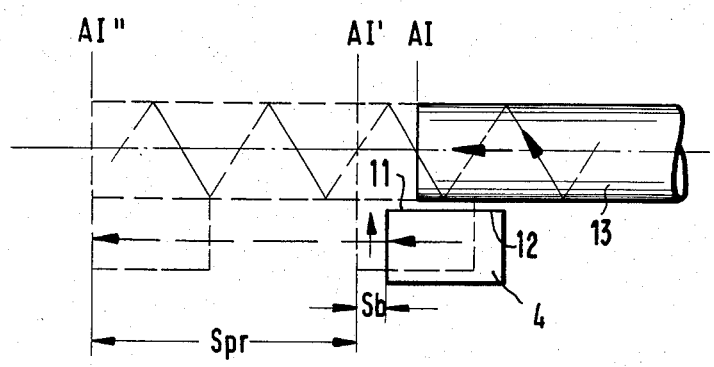
FIGS. 2a–2d shows the representation of the following, by a testing mechanism, of the path of the test material.

FIGS. 2a–2d illustrates the following of the path of the beginning and end of the test material through one of the testing mechanisms indicated in FIGS. 1a to 1c. In FIG. 2a the test material 13, rotating about its longitudinal axis, is drawing near to the testing mechanism 4. When the beginning of the test material reaches position A I, the whole testing mechanism is set in motion in the direction of transportation of the test material 13.

After a short acceleration stage $S_b$, ie. after reaching position A I', the testing mechanism 4 is raised under computer control, so that the rear end 11 of the probe or test head arrangement, accommodated in the testing mechanism, accurately engages the beginning of the test material 13.

The testing mechanism 4, which is now in contact with the test material, follows the latter with the same axial speed for the duration of at least one rotation of the test material 13 corresponding to the path of transportation $S_{pr}$ up to position A I''. Through the synchronous movement cycle of test material and testing mechanism 4, the untested wedge at the beginning of the test material 13 is avoided.

The same operation is repeated, as indicated in FIG. 1a, at the testing mechanisms 5 and 6 accommodated between the radial rolls 8,9,10.

Figure 2B:
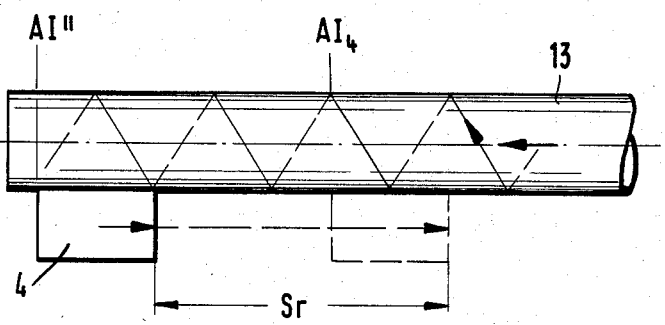

In order that the testing mechanism 4 is once again in its initial position to engage the pipe end, it must be conveyed, after reaching position A I'' according to FIG. 2b, during the further transportation of the test material, slowly in the opposite direction up to position A I$_4$ for the distance (Sr). This takes place under computer control at a speed which is proportional to the axial speed of the test material 13.

In this, the relative axial speed between the test material 13 and the testing mechanism increases. The result of this is that during the return movement of the testing mechanism, the wedge resulting from both movements increases in comparison with the wedge given through the setting of the transport mechanism. Through the selection of the magnitude of the speed of return movement, it must be ensured that the maximum permissible wedge given through the probe or test head arrangement—taking into account a certain overlap—is not exceeded. This means that after the testing mechanism has come to a standstill, ie. after position A I$_4$ has been reached, the test wedge corresponds to that given through the transport mechanism, which has a smaller value compared with the previously mentioned maximum permissible wedge.

Figure 2C:
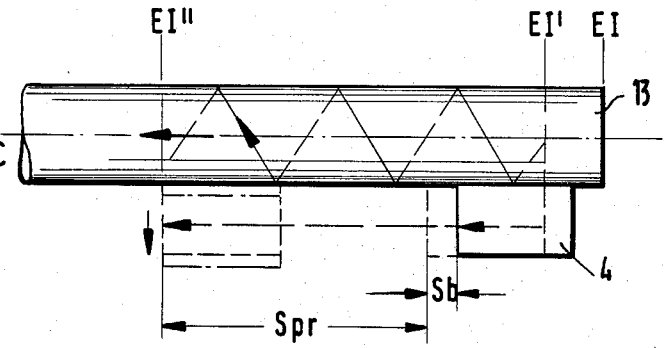

When the end of the test material according to FIG. 2c reaches position E I, the testing mechanism 4 is again set in motion in the direction of transportation of the test material. After passing through the acceleration stage Sb, the front end 12 of the probe or test head arrangement accommodated in the testing mechanism engages the end of the test material under computer control, after reaching position E I'.

The testing mechanism 4 again follows the test material 13 at the same axial speed for the duration of at least one rotation of test material 13. Here, too, because of the synchronous movement cycle no untested wedge remains.

Figure 2D:
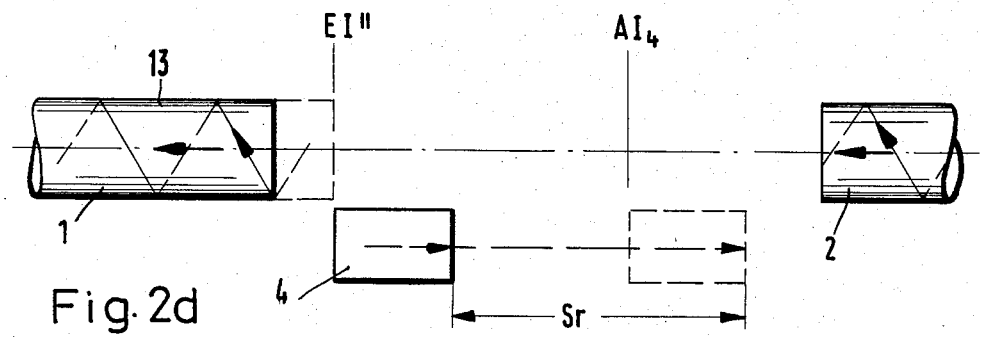

After reaching position E I'' corresponding to the travel Spr the testing mechanism 4 is lowered and returned, according to FIG. 2d at a rapid traverse rate back to its initial position A I$_4$ corresponding to the length of travel Sr, so that the testing cycle can be re-commenced on the following test sample in the same manner.

FIGS. 1a–1c show the drawing of a testing installation with three testing mechanisms 4,5,6 separate from each other, movable on sliding carriage 2. This corresponds, for example, to the layout of an ultrasonic testing installation, in which the testing levels for the measurement of longitudinal faults, transverse faults and wall thickness are accommodated in three separate testing mechanisms 4,5,6, which complete the movement cycles described in FIGS. 2a to 2d independently of each other.

The accuracy of the complete engagement of the ends of the test material depends on the accuracy to which the path of the test material 13 is followed. An exact, direct travel of the path of material transported helically is extremely costly. The indirect path travel may, for example, take place through increment formation by means of a computer from path impulses of the drive units for the transportation of the test material 13.

This proceeds from the basis of constant conditions for area per rotation of test material and slippage on drive wheels or impulse transmitters, which are in engagement with the test material. Since in practice these factors are subject to certain fluctuations, the following of the path must be checked through test marks, for example through light barriers directly in front of the individual testing mechanisms, and must be corrected if necessary.

What is claimed is:

1. A device for testing the total length of extended round material such as pipes and bars moving helically in longitudinal direction, especially with the aid of ultrasonic testing in segment immersion technique, for longitudinal and transverse faults and for wall thickness, comprising:

a plurality of testing heads, independent of each other, positioned along the longitudinal direction of the material; and driving units connected to each said testing head and moving the associated testing head as a function of the speed of movement of the material, and holding the associated testing head in contact with the forward and rearward end of the material in synchronism with the axial speed of the material at least during one revolution of the material.

* * * * *